(12) United States Patent
Tripathy

(10) Patent No.: US 10,168,527 B2
(45) Date of Patent: Jan. 1, 2019

(54) SYSTEM AND METHOD FOR SIMULTANEOUS MULTI-TUBE INSPECTION OF VERTICAL TUBE BUNDLES

(71) Applicant: Clearwater Downstream Services, LLC, Tulsa, OK (US)

(72) Inventor: Kishlay Tripathy, Friendswood, TX (US)

(73) Assignee: Clearwater Downstream Services, LLC, Tulsa, OK (US)

( * ) Notice: Subject to any disclaimer, the term of this patent is extended or adjusted under 35 U.S.C. 154(b) by 472 days.

(21) Appl. No.: 14/805,936

(22) Filed: Jul. 22, 2015

(65) Prior Publication Data

US 2016/0025961 A1 Jan. 28, 2016

Related U.S. Application Data

(60) Provisional application No. 62/027,480, filed on Jul. 22, 2014.

(51) Int. Cl.
| | |
|---|---|
| *H04N 9/47* | (2006.01) |
| *H04N 7/18* | (2006.01) |
| *G02B 23/24* | (2006.01) |
| *F22B 37/00* | (2006.01) |
| *G01N 21/954* | (2006.01) |

(Continued)

(52) U.S. Cl.
CPC ............ *G02B 23/24* (2013.01); *F22B 37/003* (2013.01); *G01N 21/8851* (2013.01); *G01N 21/954* (2013.01); *G06T 7/0008* (2013.01); *G21C 17/017* (2013.01); *G01N 2021/8854* (2013.01); *G01N 2021/9542* (2013.01); *G01N 2021/9548* (2013.01); *G06T 2207/10016* (2013.01); *G06T 2207/30108* (2013.01)

(58) Field of Classification Search
CPC .............................................. H04N 2005/2255
See application file for complete search history.

(56) References Cited

U.S. PATENT DOCUMENTS

| | | |
|---|---|---|
| 4,249,413 A | 2/1981 | Denis |
| 4,319,840 A | 3/1982 | Kondo et al. |

(Continued)

FOREIGN PATENT DOCUMENTS

| | | |
|---|---|---|
| EP | 0501648 | 9/1992 |
| JP | 2002243650 | 8/2002 |

(Continued)

*Primary Examiner* — Rebecca A Volentine
(74) *Attorney, Agent, or Firm* — Chad Hinrichs

(57) ABSTRACT

A multi-tube inspection system with a reel having a plurality of cameras is placed in the upper header. Each camera is attached to its own lead line and has a light source. An inspector, located in the upper header, aligns each camera with a tube and then operates the reel to simultaneously lower the cameras through their respective tube. As the cameras pass through the tubes, they capture a video image of the interior length of the tube. The video image is stored and relayed to a control center where additional inspectors can review the video image of the interior of the tube. Each video is identified and tied back to the tube in a data base. If a defect is identified, the tube can be taken out of service (blocked off) or scheduled for cleaning. Once cleaned, the tube is then reinspected.

6 Claims, 4 Drawing Sheets

(51) Int. Cl.
  *G21C 17/017* (2006.01)
  *G01N 21/88* (2006.01)
  *G06T 7/00* (2017.01)

(56) References Cited

U.S. PATENT DOCUMENTS

| | | | |
|---|---|---|---|
| 5,083,606 A | | 1/1992 | Brown et al. |
| 5,091,141 A | | 2/1992 | Feuillet |
| 5,105,876 A | | 4/1992 | Burack et al. |
| 5,956,135 A | * | 9/1999 | Quesnel ................ G01M 3/38 138/97 |
| 7,046,356 B2 | | 5/2006 | Bondurant |
| 7,673,496 B2 | | 3/2010 | Johns et al. |
| 8,547,428 B1 | * | 10/2013 | Olsson ................ G03B 37/005 348/374 |
| 2003/0052967 A1 | | 3/2003 | Brunton |
| 2004/0134518 A1 | * | 7/2004 | Kraus ................ B01J 8/0025 134/18 |
| 2004/0189987 A1 | | 9/2004 | Bondurant et al. |
| 2005/0126597 A1 | | 6/2005 | Hochstein, Jr. et al. |
| 2005/0183028 A1 | * | 8/2005 | Clough ................ E03F 7/12 715/771 |
| 2005/0237519 A1 | | 10/2005 | Bondurant et al. |
| 2006/0191119 A1 | | 8/2006 | Coleman et al. |
| 2007/0083398 A1 | * | 4/2007 | Ivey ................ G06Q 40/08 705/4 |
| 2008/0210024 A1 | * | 9/2008 | Merlo ................ G01M 3/047 73/865.8 |
| 2009/0095211 A1 | * | 4/2009 | Johns ................ B01J 8/0015 116/201 |
| 2010/0063304 A1 | | 3/2010 | Olbert et al. |
| 2011/0108654 A1 | * | 5/2011 | Babb ................ B65H 75/364 242/400 |
| 2012/0147173 A1 | * | 6/2012 | Lynch ................ G01N 21/954 348/84 |
| 2012/0162408 A1 | | 6/2012 | Zilberman |
| 2012/0193065 A1 | * | 8/2012 | Kawase ................ F22B 37/005 165/11.1 |
| 2014/0125791 A1 | * | 5/2014 | Arellano ................ G01N 21/47 348/82 |
| 2014/0147086 A1 | * | 5/2014 | Chapman ................ H01B 11/22 385/101 |
| 2014/0184794 A1 | | 7/2014 | Coombs et al. |
| 2014/0253715 A1 | * | 9/2014 | Hori ................ G06T 7/0008 348/82 |
| 2015/0341600 A1 | * | 11/2015 | Hatcher, Jr. ............ H04N 7/183 348/82 |

FOREIGN PATENT DOCUMENTS

| | | |
|---|---|---|
| JP | 2005201664 | 7/2005 |
| WO | 95/09323 | 4/1995 |
| WO | 95/19526 | 7/1995 |

* cited by examiner

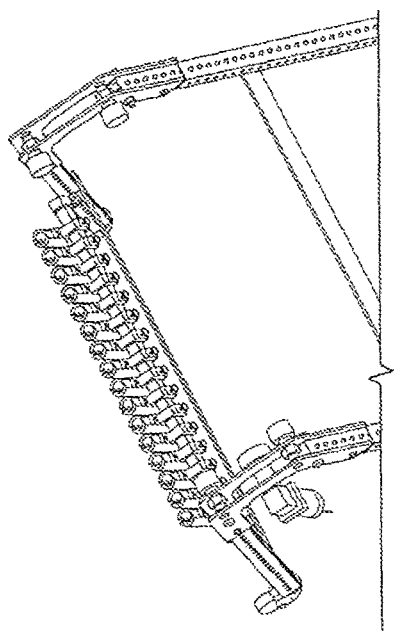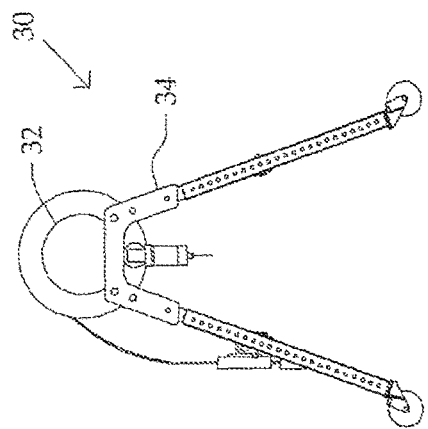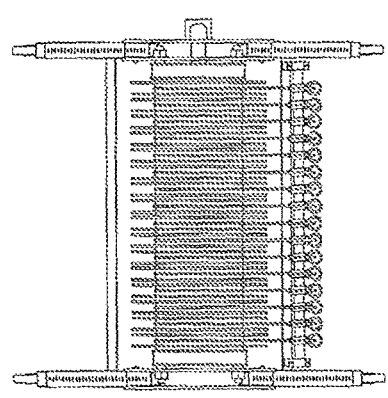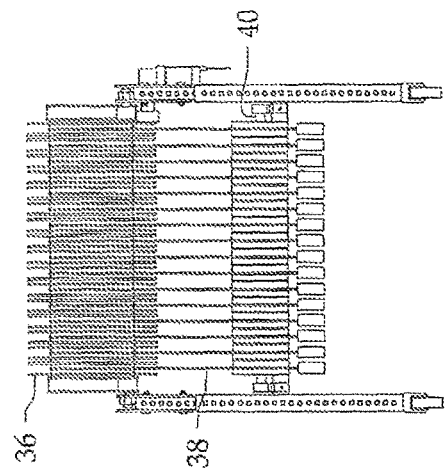

SYSTEM AND METHOD FOR SIMULTANEOUS MULTI-TUBE INSPECTION OF VERTICAL TUBE BUNDLES

PRIORITY CLAIMS

The present application is a continuation-in-part of U.S. Provisional Patent Application No. 62/027,480 entitled "System and Method for Multi-Tube Inspection of a Tubular Reactor" filed on Jul. 22, 2014 which is incorporated herein by reference.

FIELD OF THE INVENTION

The present invention relates generally to visual inspection of tubes in a vertical tube bundle. More particularly, the present invention relates to simultaneous visually inspection of multiple vertical tubes of a tubular reactor.

BACKGROUND OF THE INVENTION

The safe operation of reactors, boilers and other pressure vessels requires the regular inspection of the vessel and its interior parts. In the case of pressure vessels with tube bundles, each tube must be examined for scaling, cracks or ruptures. For certain types of vessels such as ethylene oxide reactors, the tube bundles are oriented vertically. Thus, the inspection requires an individual in the lower head to shine a light through each individual tub while a second individual looks down that same tube to identify any defects or plugging. If defects are located, the tube can be blocked off at the top and bottom ends or marked for cleaning or other treatment. Once cleaned, the tube must be reinspected.

These tube bundles are typically forty feet long or longer and contain thousands of tubes. The inspection service, even without cleaning and reinspection, is extremely time consuming. Plus, small cracks at the far end of the tube can be difficult to see. This is further complicated by identifying and locating tubes to be cleaned and reinspected.

Taking one of these vessels out of service can cost hundreds of thousands, and in some cases, millions of dollars a day. This provides a huge incentive to work as quickly as possible. This time pressure can lead to further inaccuracies in the work.

What is needed is a way to speed up and increase the accuracy of these inspections.

BRIEF SUMMARY OF THE INVENTION

The present invention achieves its objectives by providing a system and method for simultaneously inspecting multiple tubes in these vertical tube bundles. The pressure vessel is taken out of service and the catalyst and any other structures are removed from the tube bundle. A multi-tube inspection system with a reel having a plurality of cameras is placed in the upper header. Each camera is attached to its own lead line and has a light source. An inspector, located in the upper header, aligns each camera with a tube and then operates the reel to simultaneously lower the cameras through their respective tube. As the cameras pass through the tubes they capture a video image of the interior length of the tube. The video image is stored and relayed to a control center where additional inspectors can review the video image of the interior of the tube. Each video is identified and tied back to the tube in a data base. If a defect is identified, the tube can be taken out of service (blocked off) or scheduled for cleaning. Once cleaned, the tube is then reinspected.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

FIG. 6 is a top view of the multi-tube inspection system;

FIG. 7 is a front view of the multi-tube inspection system;

FIG. 8 is an end view of the multi-tube inspection system; and

FIG. 9 is an end view of the base of the multi-tube inspection system.

DETAILED DESCRIPTION OF THE INVENTION

Figure 1:
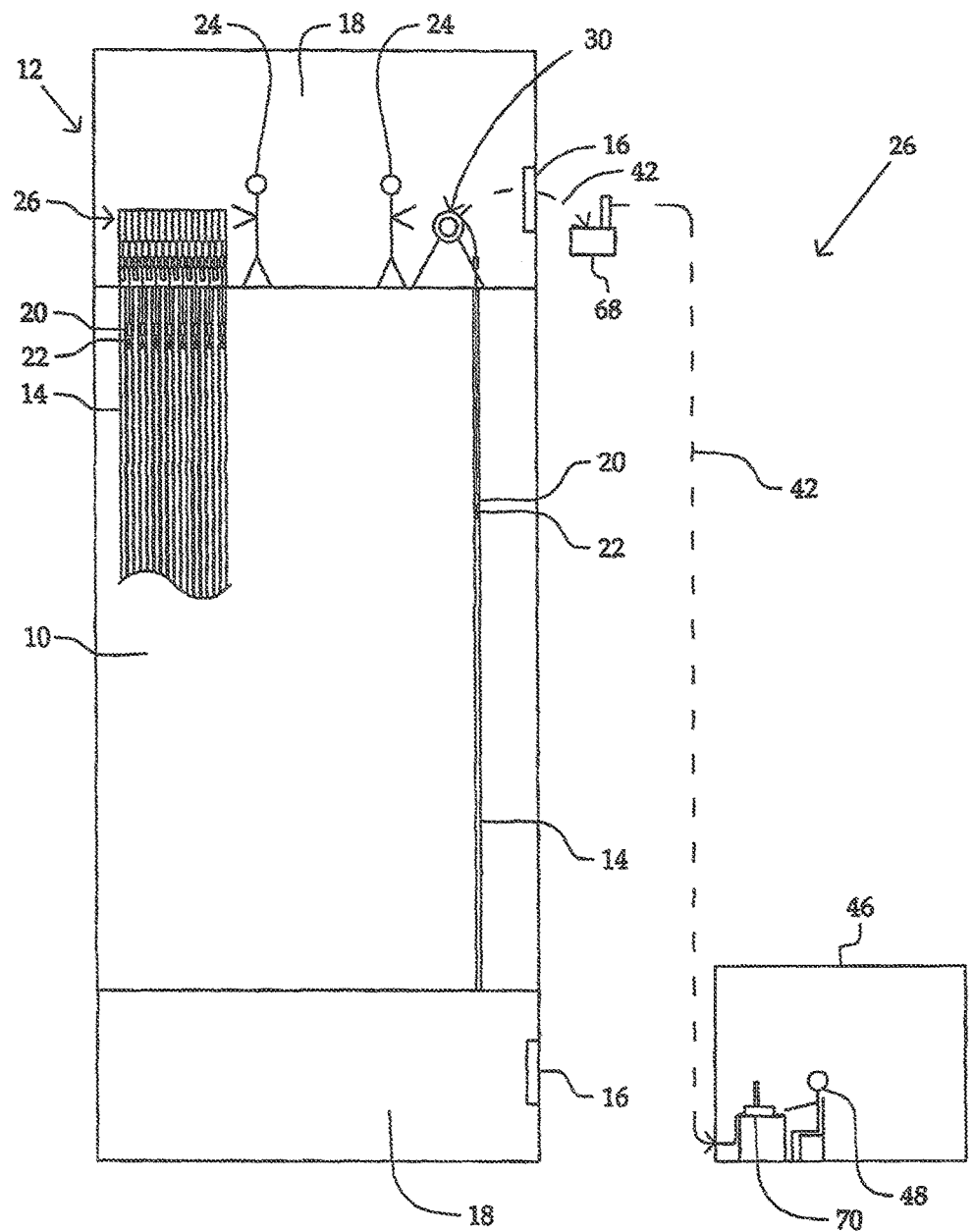
FIG. 1 is a schematic view showing the multi-tube inspection process and system.
Figure 2:
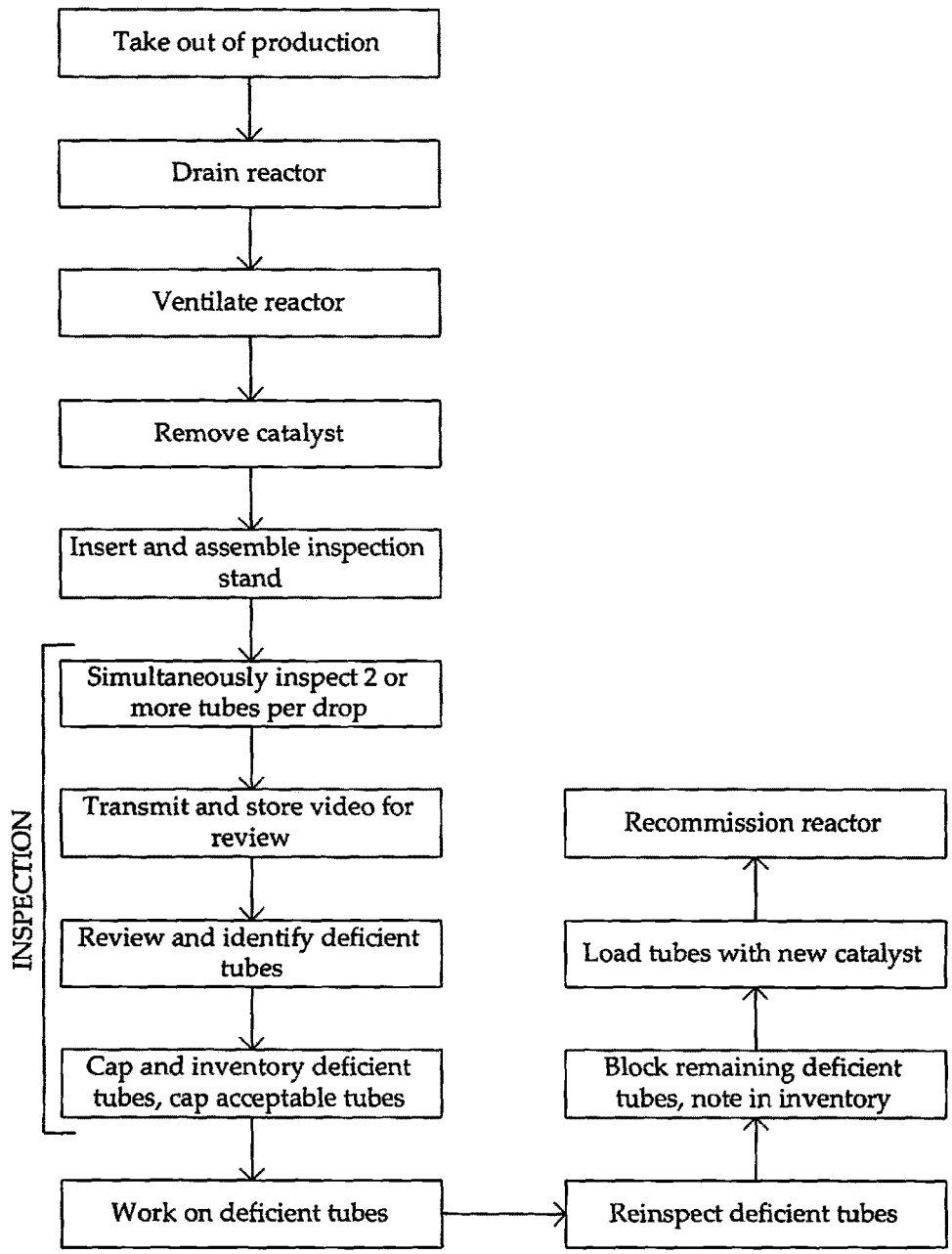
FIG. 2 is a flow diagram showing the multi-tube inspection process.

Turning now to the drawings wherein like reference characters indicate like or similar parts throughout, FIG. 1 is a schematic of the system and method of the present invention for inspecting vertically oriented tube bundles 10 typically found in tubular reactors 12. A typical reactor 12 may have as many as 5,000 to 10,000 individual tubes 14. These tubes 14 are typically 20 to 40 feet in length with manway 16 access to the headers 18 at the top and bottom of the tube bundle 10. The area and volume in these headers 18 vary but are typically large enough to hold two to four inspectors and the equipment disclosed in this application.

During operation, these tubes 14 contain catalyst. Various petroleum products flow through these tubes 14 where the product is further refined through reaction with the catalyst. The reactors 12 are taken out of production on a periodic basis to remove the used catalyst, inspect and repair damaged tubes 14 and then refilled with new catalyst. The present invention includes an inspection process of simultaneously lowering a plurality of cameras 20, each with a light source 22, down a plurality of tubes 14 in the bundle 10. Thus, each camera 20 passes through a separate tube 14.

Once the reactor 12 is taken out of service, the remaining petrochemicals are drained. The manways 16 to the upper and lower headers 18 are opened and the reactor 12 is ventilated. Crews then enter the headers 18 and remove the catalyst from the tubes 14. This is accomplished in a manner known in the industry.

With the tubes 14 empty, the inspection crew consisting of one or more inspectors 24, each with a multi-tube inspection system 26, enter the upper header 18. The legs 28 of the stand 30 and drum 32 can be removed from the base 34, if needed, to fit it through the manway 16. Once inside, the stand 30, drum 32 and cameras 20 are assembled on the base 34. The inspector 24 then lowers two or more cameras 20 down two or more tubes 14. In other words, each of the two or more tubes 14 being inspected has a camera 20 and light source 22 passing through it. The preferred embodiment shows 16 individual reels 36 each with its own camera 20, light source 22 and lead line 38. The drum 32 is rotated allowing the cameras 20 and light source 22 to lower each through an individual tube 14 as the lead lines 38 are unspooled from their individual reels 36 and pass through the adjustable guide jig 40. The drums 32 are mounted on a common axis 72 such that rotation of one drum 32 causes rotation of the other drums 32 on the axis 72.

As the cameras 20 are lowered through their respective tubes 14, the video signal 42 is transmitted up the lead lines 38 to the camera control unit 44. The video signal 42 is then transmitted, preferably wirelessly, to a control center 46 where the video footage of the tubes 14 can be examined by a supervising technician or engineer 48. Based on the video, if a tube 14 is determined to need further work to remedy a problem, it is blocked with a cap 50 which has an RFID marker 52 that is assigned a unique identifier 54. A database 56 can then be maintained to identify the exact tube 14 and its deficiencies. Tubes 14 that are deemed acceptable are provided with a cap 50 which may not have an RFID marker 52. The caps 50 of the deficient and acceptable tubes 14 may be further differentiated by using different colored caps 50, such as red for deficient tubes 14 and green for acceptable tubes 14.

When a deficient tube 14 has been worked on to remove the deficiency, it is re-inspected. If the deficiency has been resolved, the tube 14 receives a green cap 50 and the correction is noted in the database 56. If the deficiency remains, the red cap 50 is reinstalled. The further deficiency is noted in the database 56. The tube 14 may receive further work and re-inspection or be taken out of service. In order to take a tube 14 out of service, both ends of the tube 14 must be blocked off to prevent liquids from entering the tube 14.

The multi-tube inspection system 26 has a stand 30 with a base 34 having removable legs 28. The length of the legs 28, and in turn, the height of the stand 30 can be adjusted. A drum 32 having a plurality of reels 36 is rotatably mounted on the stand 30. In the preferred embodiment shown in the drawings, this rotatable mounting is accomplished by the drum 32 riding on a plurality of rollers 58. Thus, the drums 32 have a common axis of rotation 72. The drums 32 are also engaged with a variable speed drive motor 60. When energized, the variable speed drive motor 60 causes the drums 32 to rotate about the axis of oration 72. It should be noted that the drums 32 could be rotatably mounted to the stand 30 in other ways. Further, the rotation of the drum 32 could be induced by other mechanisms, including but not limited to, being manually rotated by hand.

Each reel 36 has a lead line 38 that electronically connects a camera 20 and light source 22 to a power source 62. It also provides a path for the video signal 42 from the camera 20 to the camera control unit 44. Each lead line 38 passes though one of the guides 64 on the guide jig 40 as it is raised and lowered. The guides 64 can be adjusted along the guide jig 40 to match the spacing between the tubes 14 in the tube bundle 10.

Figure 4:
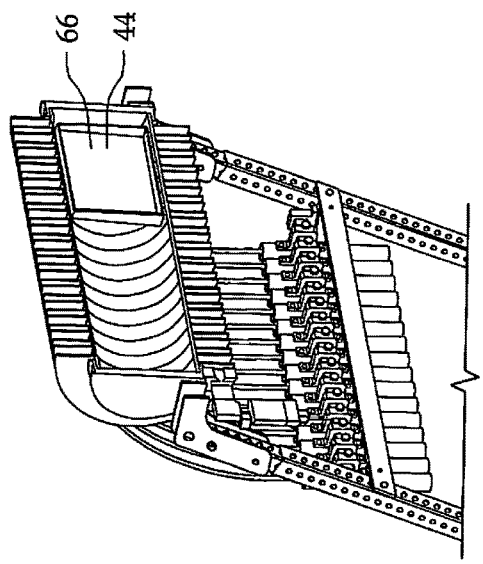
FIG. 4 is a sectional view of the multi-tube inspection system.
Figure 3:
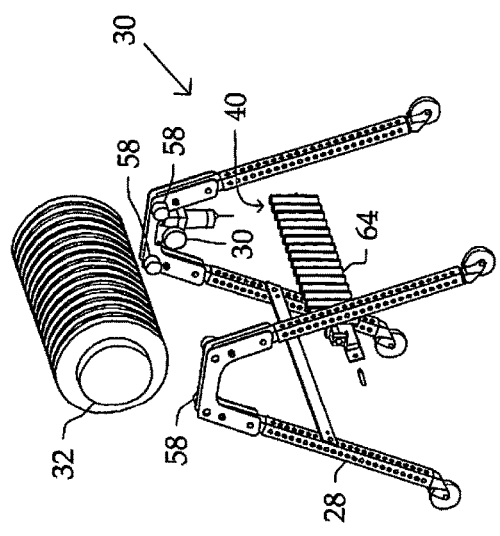
FIG. 3 is an exploded view of the multi-tube inspection system.
Figure 5:
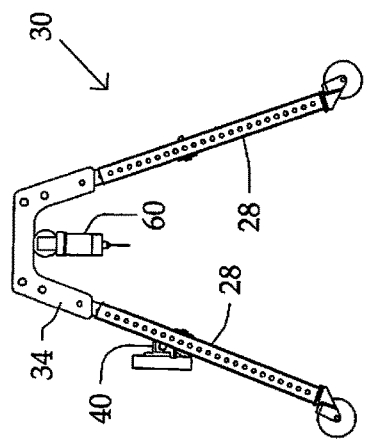
FIG. 5 is an end view of the base of the multi-tube inspection system.

As best seen in FIG. 4, in the preferred embodiment, the camera control unit 44 and battery 66 are located inside the drum 32. This keeps the system 26 as compact as possible. The battery 66 provides power to the cameras 20, light sources 22, variable speed drive 60 and camera control unit 44. The camera control unit 44 provides DVR storage of the video signal 42. It also provides a Wi-Fi or other wireless connection to the control center 46. In some applications, it may be necessary to provide a wireless router 68 or repeater just inside or just outside the manway 16 in order to get the wireless signal to the control center 46.

The video signal 42 of each tube 14 inspected is reviewed on a computer 70 or other video display device by a supervising engineer or technician 48 in the control center 46.

Additional features to the present invention may include, but are not limited to, the use of a Unique Tube Identification Software (UTIS). The UTIS software, will assist in generating reports for each inspected tube. This may include listing of physical tube asset management or unique address, tube conditions, residue identification, rust and hot spot locations on each tube. The report may also include the location of the defect or abnormality within the tube.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. A method for inspecting a vertical tube bundle containing catalyst in a reactor, the method comprising:
   taking the reactor out of service;
   draining the tube bundle;
   placing a multi-tube inspection system and an inspector within the reactor in a header above the tube bundle;
   simultaneously lowering a plurality of cameras through a plurality of tubes in the tube bundle, wherein each camera passes through a separate tube; and
   capturing a video image of the interior of each tube of the plurality of tubes through which the cameras pass.

2. The method of claim 1 further comprising removing the catalyst from the tube bundle.

3. The method of claim 1 further comprising:
   transmitting the video image to a control room where it is reviewed by an inspector; and
   identifying defects in the plurality of tubes.

4. The method of claim 3 further comprising:
   listing in a database the defects identified; and
   correlating the defects identified with a tube in which the defect is located.

5. The method of claim 4 further comprising:
   storing the video of the interior of the plurality of the tube;
   correlating the video with the tube from which it was taken; and
   recording in the database the correlation between the video and the tube.

6. The method of claim 5 further comprising:
   blocking off tubes containing defects;
   repairing the tube containing the defect;
   reinspecting the tube containing the defect; and
   recording in the database the defect, tube containing the defect and a final status after reinspecting.

\* \* \* \* \*